(12) United States Patent
Dellimore et al.

(10) Patent No.: US 8,784,909 B2
(45) Date of Patent: Jul. 22, 2014

(54) MUD MASK WITH REAL TEA LEAF AND METHOD FOR MAKING THE SAME

(75) Inventors: Shannon Beth Dellimore, Encino, CA (US); Glenn Dellimore, Encino, CA (US)

(73) Assignee: Glamglow, Inc., Hollywood, CA (US)

( * ) Notice: Subject to any disclaimer, the term of this patent is extended or adjusted under 35 U.S.C. 154(b) by 514 days.

(21) Appl. No.: 13/101,055

(22) Filed: May 4, 2011

(65) Prior Publication Data

US 2012/0282355 A1    Nov. 8, 2012

(51) Int. Cl.
| | | |
|---|---|---|
| *A61K 36/82* | (2006.01) | |
| *A61K 31/785* | (2006.01) | |
| *A61K 8/97* | (2006.01) | |
| *A61K 8/02* | (2006.01) | |
| *A61K 8/96* | (2006.01) | |

(52) U.S. Cl.
CPC . *A61K 8/965* (2013.01); *A61K 8/97* (2013.01); *A61K 8/0212* (2013.01); *A61K 36/82* (2013.01)
USPC ...................................... 424/729; 424/78.03

(58) Field of Classification Search
None
See application file for complete search history.

(56) References Cited

FOREIGN PATENT DOCUMENTS

| | | |
|---|---|---|
| CN | 101 416 928 | 4/2009 |
| KR | 20010089937 | 10/2001 |
| KR | 2005024742 A * | 3/2005 |
| KR | 100 800 316 | 2/2008 |
| WO | WO 98/41096 | 9/1998 |
| WO | WO 2005/027867 | 3/2005 |

OTHER PUBLICATIONS

Database GNPD [Online] MINTEL; Aug. 2009, "Skin clearing blemish mud," XP002692723, Database access No. 1150517.
Database GNPD [Online] MINTEL; Jan. 2008, "Facial peel," XP002692742, Database accession No. 846064.
PCT International Search Report and Written Opinion of the International Searching Authority for PCT/US2012/000085, date of mailing Mar. 13, 2013.
Database GNPD [Online] MINTEL; Mar. 2011, "Mud Mask," XP002692717, Database accession No. 1517786.
Database GNPD [Online] MINTEL; Oct. 2002, "Miwa-Chacha skin pack," XP002692718, Database accession No. 170087.
"Green Tea Face Mask," Mar. 12, 2009, XP002692719, Retrieved from the Internet: URL:http//anindiansmakeupmusings.blogspot [retrieved on Feb. 25, 2013].
McConnel M.: "Macha for your skin." Dec. 18, 2009, XP002692720, Retrieved from the Internet: URL:http://www.machomatcha.com/everyday-matcha/matcha-for-your-skin [retrieved on Feb. 22, 2013].
Database WPI, Week 200940, Apr. 29, 2009, Thomson Scientific, London, GB; AN 2009-J02105, XP002692721.
Database GNPD [Online] MINTEL; Jan. 2010, "Facial Mask," XP002692722, Database accession No. 1248756.

* cited by examiner

*Primary Examiner* — Chris R Tate
*Assistant Examiner* — Deborah Davis
(74) *Attorney, Agent, or Firm* — Tope-McKay & Associates

(57) ABSTRACT

A mud mask with real green tea leaves is described. The mud mask is made by separating a real green tea leaf batch into a first sub-batch, a second sub-batch, and a third sub-batch. The first sub-batch is ground into a fine powder, while the second sub-batch remains as whole leaves and the third sub-batch is chopped into partially chopped leaves. The fine powder and whole leaves are added to hot water for a period of time to form a brewed tea. Thereafter, the partially chopped leaves and mud components are added to the brewed tea to form a mud solution, which is mixed to form the mud product. The mud product is packaged and allowed to marinate, which allows the leaves to begin releasing their nutrients and antioxidants into the mud formula, after which the mud mask includes atypical and unusually high levels of nutrients, antioxidants and caffeine.

8 Claims, 3 Drawing Sheets

MUD MASK WITH REAL TEA LEAF AND METHOD FOR MAKING THE SAME

BACKGROUND OF THE INVENTION (1) Field of Invention

The present invention relates to a mud mask and, more particularly, to a and mask having real green tea leaf therein and a method for making the same.

(2) Description of Related Art

Since ancient times, people have flocked to mud pools and used other forms of mud treatments for therapeutic and relaxing effect. Such mud treatments are often used as facial masks that are applied to clean and/or smooth a user's face. The perceived effect of a facial mask treatment can be revitalizing, rejuvenating or refreshing and can serve temporary or long term benefits depending on its usage.

While other types of creams are often used as facial masks, mud masks provide a thicker consistency and will dry to pull out impurities from the pores, while a creamier mask stays damp to hydrate the skin. Alternatively, other masks are formed as a combination of mud and cream to include small sandy beads for exfoliating the skin. These different masks are made to suit different skin types such as oily or dry, as well as the different needs of the skin, whether it be moisturizing, cleansing, or exfoliating. Traditionally, mud masks suit oily skin while cream based masks suit dry skin types.

As an improvement over traditional mud masks, recent innovation has led to mud mask having various components added therein (e.g., minerals and extracts) to provide additional therapeutic effect. By way of example, mud masks have been devised that include green tea extract. Real green tea extract or (EGCG) (epigallocatechin gallate) is a powerful antioxidant that is used to rid skin of impurities.

Adding the green tea extract to a mud mask product during production provides an immediate and one-time infusion of antioxidants. Thereafter, the mud mask product is sealed and typically shelved for weeks, months or years, after which it is used by an end consumer. While operable for a one-time infusion of antioxidants, existing mud masks do not provide for a continuous release of fresh and new natural nutrients and antioxidants to the mud formula after the product is sealed for retail distribution and sale. Efficacy of nutrients and antioxidants diminish over time, affecting the results of the any such products.

Thus, a continuing need exists for a mud mask product that provides a natural nutrient and antioxidant "time-release" system for delivering fresh and new natural nutrients and antioxidants to the mud product after sealing for retail. The non obvious invention of "time-release" is a "game changer" within the realm of the huge number (possibly 100's) of cosmetic skincare mud masks in the retail market and from the early period conception of retail mud masks.

SUMMARY OF INVENTION

As noted above, existing mud masks do not provide for a continuous "time-release" of new natural nutrients and antioxidants to the mud product. Thus, while considering the failure of others to make use of all of the above ingredients in this technology space, the inventors unexpectedly realized that using real, brewed green tea leaves of varying sizes, combined with mud components, would result in a unique mud mask that provides for a continuous release of fresh and new nutrients and antioxidants, after the product is sealed for retail distribution and sale.

As such, the present invention is directed to a unique mud mask and a method of forming the same. The mud mask is made by separating a real green tea leaf batch into a first sub-batch, a second sub-batch, and a third sub-batch. The first sub-batch is ground into a fine powder, while the second sub-batch remains as whole leaves and the third sub-batch is chopped into partially chopped leaves. The fine powder and whole leaves are added to hot water for a period of time to form a brewed tea. Thereafter, the partially chopped leaves (non-brewed real green tea leaves) and mud components are added to the brewed tea to form a mud solution, which is mixed to form the mud product. The mud product is then packaged and sealed in retail packaging and allowed to marinate for a marinating period (e.g., three days) before authorized for retail sale. The marinating period allows the leaves to begin slowly releasing their nutrients and antioxidants into the mud product to cause the mud product to have atypical and unusually high levels of nutrients, antioxidants and caffeine.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
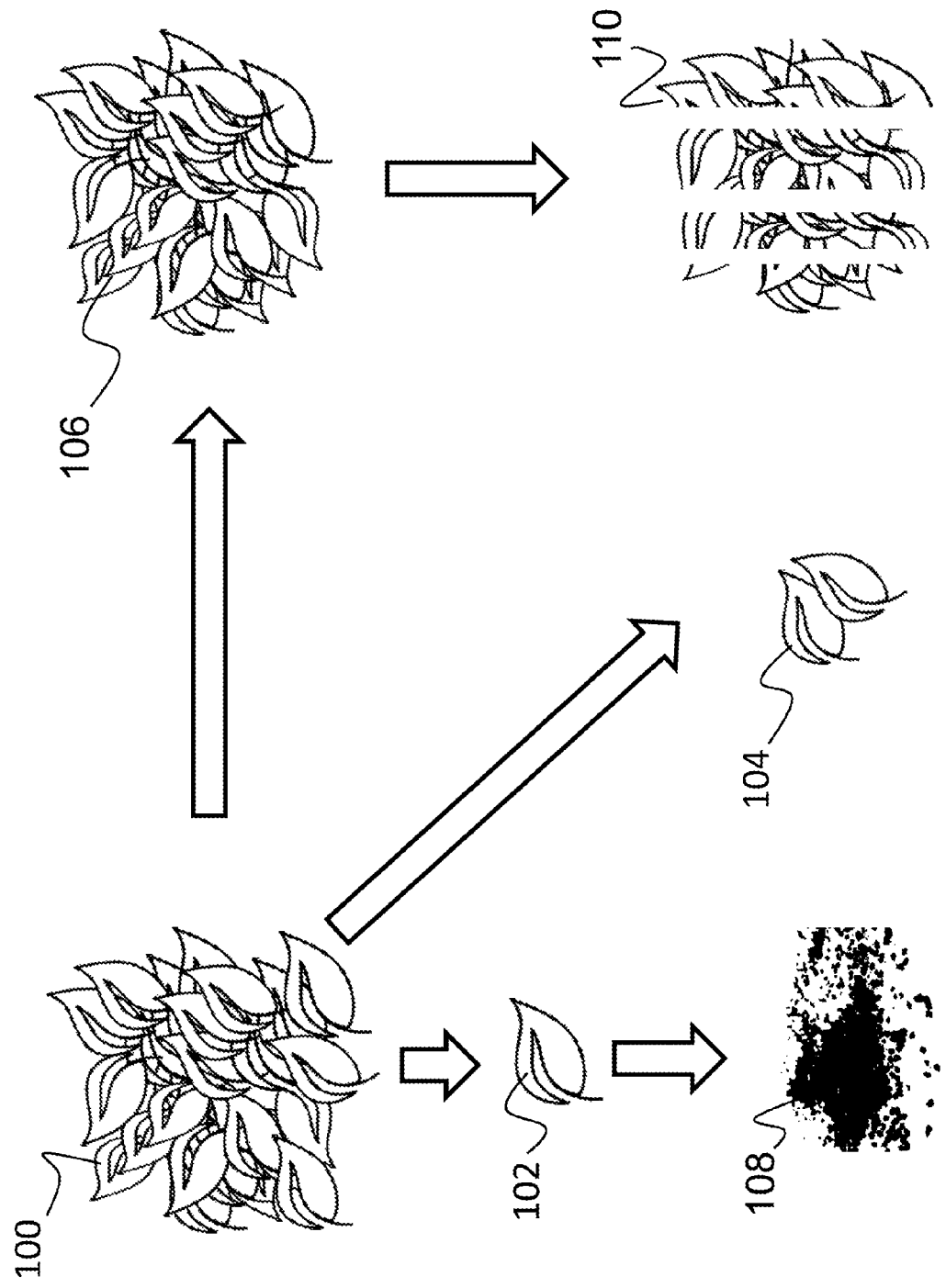
FIG. 1 is an illustration depicting a separation of green tea leaves into three sub-batches.

The present invention relates to a mud mask and, more particularly, to a mud mask having real green tea leaf therein and a method for making the same. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

(1) Description

The present invention relates to a mud mask with brewed, real green tea leaf and a corresponding method for making such a mud mask. Due to its unique composition and method of formulation, the mud mask of the present invention provides a natural nutrient and antioxidant "time-release" system for delivering fresh and new natural nutrients and antioxidants to the mud formula after sealing for retail. The present invention provides a unique ability to "time-release" nutrients and antioxidants from the green tea leaf. This is accomplished by combining different size parts of tea leaves in the unique compound viscosity of mud, which slows down the short term and long term release of nutrients and antioxidant, thereby creating a completely unique method of treatment delivery over time.

As noted above, the present invention includes a unique method for forming the mud mask. For a better understanding, the method is described in detail below.

First, and as depicted in FIG. 1, a real green tea leaf batch 100 is collected. The real green tea leaf batch 100 has an initial mass (or volume) that is separated into three sub-batches, a first sub-batch 102, a second sub-batch 104, and a third sub-batch 106. The three sub-batches are separated into any suitable volume or mass ranges. As a non-limiting example, the first sub-batch 102 has a mass that is between zero percent and ten percent of the initial mass, while the second sub-batch 104 has a mass that is between zero percent and fifteen percent of the initial mass, and the third sub-batch 106 has a mass that is approximately between fifty and one hundred percent the initial mass.

Desirably, the first sub-batch 102 has a mass that is approximately one percent (1.0%) of the initial mass, while the second sub-batch 104 has a mass that is approximately one and one quarter percent (1.25%) of the initial mass, and the third sub-batch 106 has a mass that is approximately ninety seven and three quarters percent (97.75%) of the initial mass.

After generating the various sub-batches, each sub-batch is treated slightly differently. The first sub-batch 102 is ground into a fine powder 108, while the third sub-batch 106 chopped to form partially chopped leaves 110. Alternatively, the second sub-batch 104 remains as whole leaves.

Figure 2:
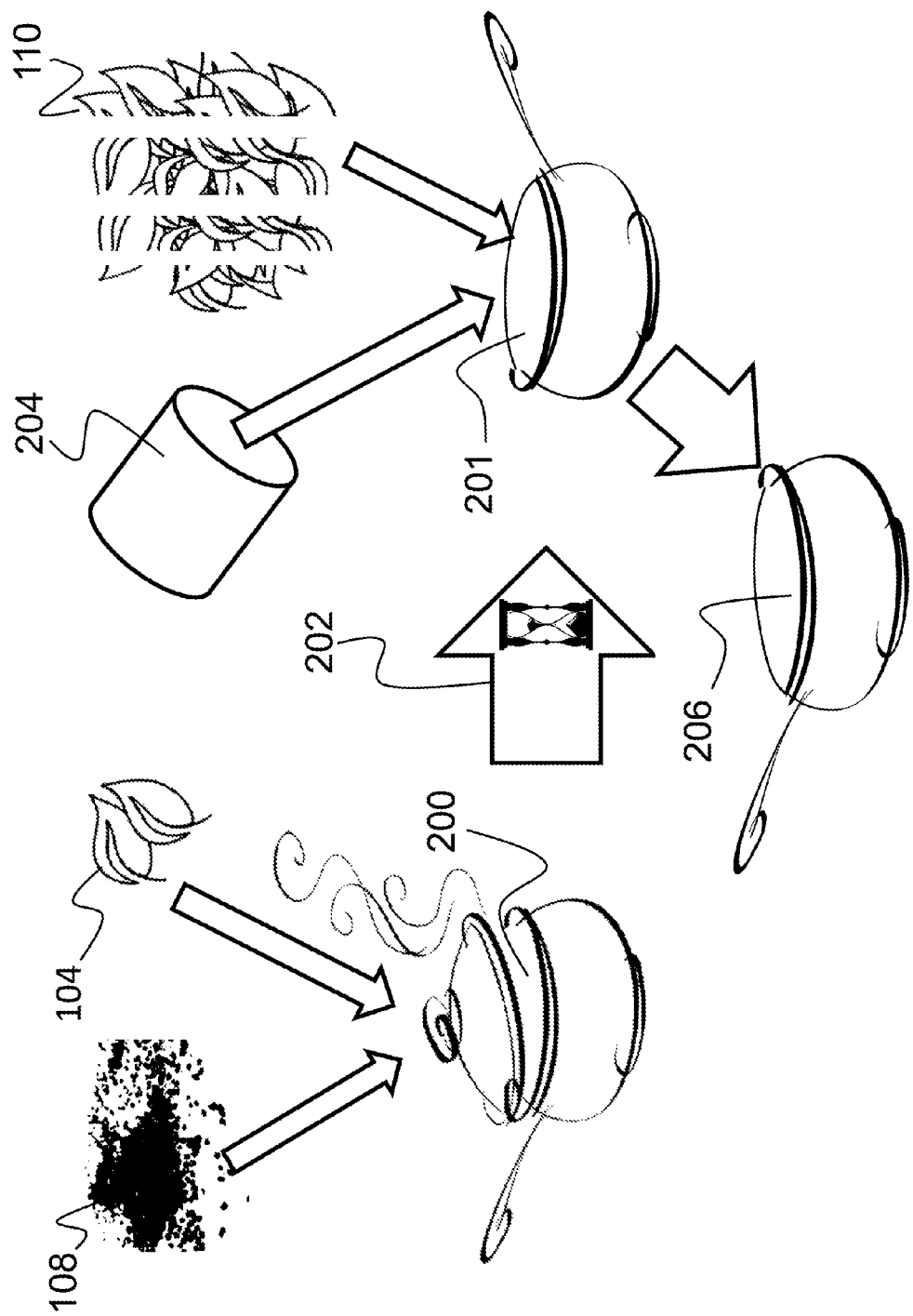
FIG. 2 is an illustration depicting the formation of a mud solution.

A unique aspect of the present invention is its brewing process of actually brewing the green tea leaves, which are then added to a mud formula. As a non-limiting example and as shown in FIG. 2, water 200 (e.g., de-ionized water) is heated. For example, the water 200 is heated to approximately 40 degrees Celsius (or any other suitable temperature for brewing tea). To brew the green tea, the fine powder 108 and the second sub-batch 104 (i.e., whole, ungrounded leaves) are added to the water 200 and sealed for a period of time 202 to create a brewed tea 201. As a non-limiting example, the components are sealed for approximately ten (10) minutes. Although it is not required, the components are sealed to prevent water loss. The fine powder 108 provides an immediate and intense "short-term" release of nutrient and antioxidant rich tea partials, which are dispersed evenly throughout the brewed tea 201 which is later used for the mud formula, while the second sub-batch 104 provides a slow, "long-term" release of nutrients and antioxidant rich tea partials.

After the period of time 202, the partially chopped leaves 110 and mud components 204 are slowly added to the brewed tea 201 to form a mud solution 206. The mud components 204 include mud and any suitable ingredient to provide a therapeutic effect to the mud solution 206. Non-limiting examples of such ingredients include Montmorillonite, Kaolin, Magnesium Aluminum Silicate, Camellia Oleifera (Green Tea) Leaf Extract, Lavandula Hubrida, Lavender Oil, Diazolidinyl Urea, Phenoxyethanol, Methylparaben, Butylparaben, Ethylparaben, Propylparaben, Isobutylparaben, Glycerin, Chamomilla Recutita (Chamomile) Flower Extract, Calendula Officinalis Flower Extract, Cucumis Sativus (Cucumber) Fruit Extract, Hedera Helix (Ivy) Extract, Symphytum Officinale (Comfrey) Leaf Extract, Camellia Sinensis Leaf, Pumice, and Inducos.

Although not limited thereto, the mud solution 206 is desirably made of approximately ten percent (10.0%) real green tea leaf (from the fine powder 108, second sub-batch 104, and the partially chopped leaves 110) and ninety percent (90%) of mud components 204.

Figure 3:
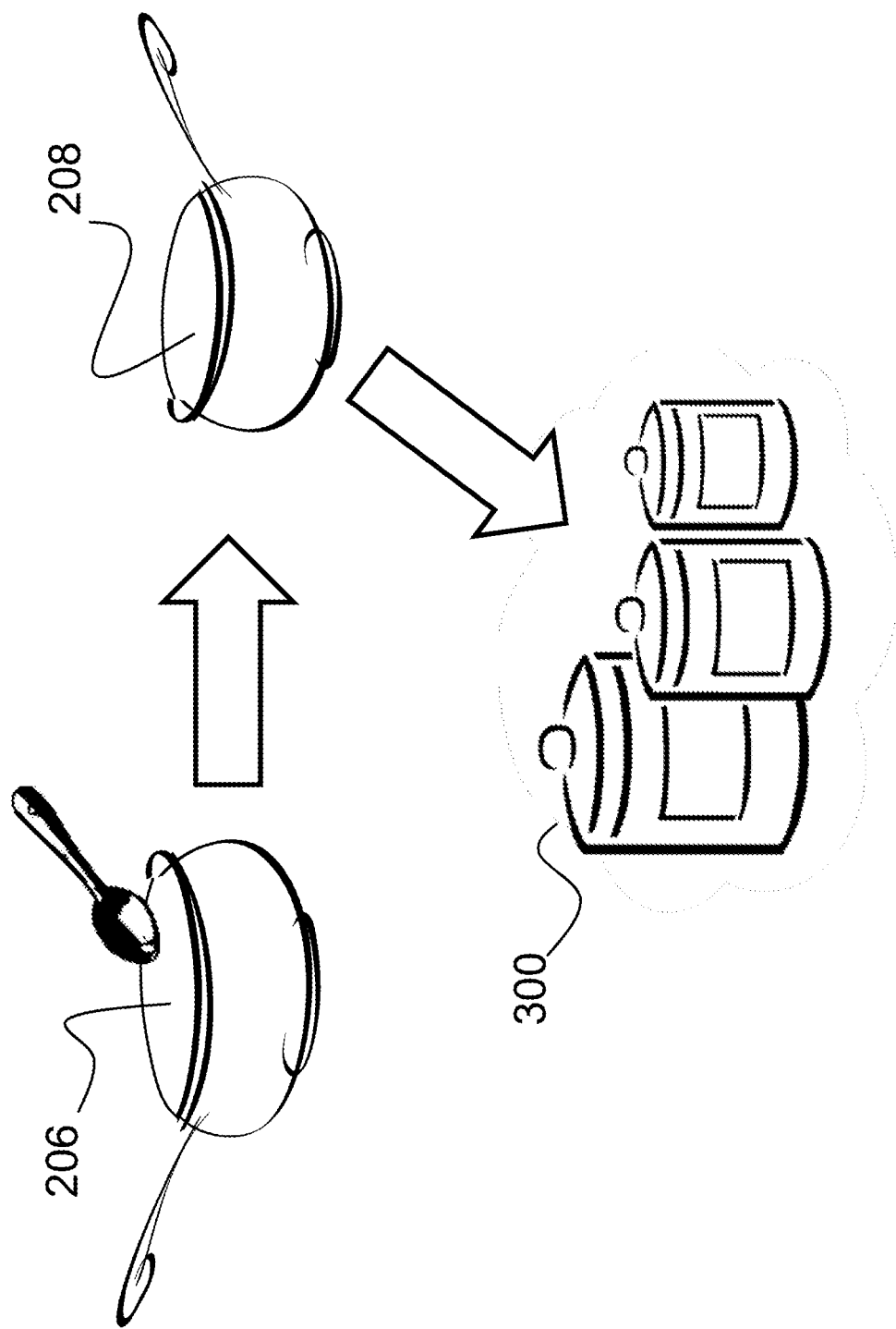
FIG. 3 is an illustration depicting the formation of a mud mask according to the present invention.

As shown in FIG. 3, the mud solution 206 is then mixed until the batch is a uniform mud product 208. The uniform mud product 208 is thereafter packaged and sealed in retail packaging 300. As noted above, the fine powder provides an immediate and intense "short-term" release of nutrient and antioxidant rich tea partials, while the second sub-batch (whole leaves) provides a slow, "long-term" release of nutrients and antioxidant rich tea partials through the thick leaf membrane and thick stems in the mud product 208.

Although the mud product 208 is sealed in retail packaging 300, a marinating period (e.g., three days) is maintained before the mud product 208 is released for retail. During the marinating period, the mud product darkens as the fine powder releases all of its nutrients and antioxidants into the mud formula and as the partially chopped leaves begin releasing their nutrients and antioxidants into the mud formula. After the marinating period (e.g., three days), the mud includes atypical and unusually high levels of nutrients, antioxidants and caffeine, thus providing a consumer with a mud mask that, when used, provides a natural tingling/light burning sensation. Such an effect (i.e., tingling/light burning sensation) is not present when the mud formula is first manufactured and packaged.

After the marinating period, the mud product will continue to slightly darken over a few months as the remaining whole tea leaves (i.e., second sub-batch) (after the thick leaf membrane and thick stem in the water 200) release small quantities of remaining nutrients and antioxidants left in the thicker membrane leaf and stems.

Thus, the end mud mask is a mud product that includes approximately 10.0% real green tea leaves and approximately 90.0% of mud components. The real green tea leaves are comprised of approximately 1.0% of fine powder, 1.25% of whole, ungrounded green tea leaves (i.e., second sub-batch), and 97.5% of partially chopped leaves.

It should be understood that the percentages listed above and described herein are provided as but one non-limiting example of a desirable composition, as the present invention is not intended to be limited thereto. Thus, as can be appreciated, each of the percentages listed herein can be varied (for example, within ranges of 5.0% or any other suitable percentage) to accomplish a mud mask according to the present invention. As a non-limiting example, instead of 90.0% of mud components, the mud components being a range of 85.5% to 95.5% of the mud product, while the real green tea leaves can be in the range of 5.0% to 15.0%. Of the real green tea leaves, the fine powder can be in a range of 0% to 6%, the whole, ungrounded leaves can be in a range of 0% to 6.25%, and the partially chopped leaves can be in a range of 92.5% to 100%.

Further, although the invention is described as being used with green tea leaves, the invention is not limited thereto as other-products can be used. For example, mint leaves, plants, fruit, and vegetables can be brewed in place of or in conjunction with the green tea leaves and mixed into a natural 'time-release' blend mud mask.

What is claimed is:

1. A method for making a packaged green tea mud mask product comprising:
    forming a green tea mud mask product; and
    packaging and sealing the green tea mud mask product in retail packaging;
        wherein said forming the green tea mud mask product comprises:
    separating a green tea leaf batch of whole leaves into three sub-batches, a first sub-batch, a second sub-batch, and a third sub-batch;
    grinding the first sub-batch into a fine powder;
    chopping the third sub-batch into partially chopped leaves;
    heating water;
    adding the fine powder and second sub-batch to the heated water for a period of time to form a brewed tea;
    adding, after the period of time, the partially chopped leaves and mud to the brewed tea to form a mud solution; and
    mixing the mud solution to form the green tea mud product.

2. The method as set forth in claim 1, further comprising marinating the green tea mud mask product for a marinating period.

3. The method as set forth in claim 2, wherein the green tea leaf batch has an initial mass, with the first sub-batch having a mass that is approximately one percent (1.0%) of the initial mass, while the second sub-batch has a mass that is approximately one and one quarter percent (1.25%) of the initial mass, and the third sub-batch has a mass that is approximately ninety seven and three quarters percent (97.75%) of the initial mass.

4. The method as set forth in claim 3, wherein green tea leaves comprise approximately ten percent by volume of the green tea mud product while the mud comprise approximately ninety percent by volume of the green tea mud product.

5. A green tea mud mask product prepared by the method according to claim 1.

6. The green tea mud mask product as set forth in claim 5, wherein the green tea mud mask product has been marinated for a marinating period.

7. The green tea mud mask product as set forth in claim 6, wherein the green tea leaves collectively have an initial mass, such that the fine powder has a mass that is approximately one percent (1.0%) of the initial mass, while the whole green tea leaves have a mass that is approximately one and one quarter percent (1.25%) of the initial mass, and the partially chopped green tea leaves have a mass that is approximately ninety seven and three quarters percent (97.75%) of the initial mass.

8. The green tea mud mask product as set forth in claim 7, wherein green tea leaves comprise approximately ten percent by volume of the mud product while the mud comprise approximately ninety percent by volume of the mud product.

* * * * *